United States Patent

Heinonen et al.

[11] Patent Number: 5,983,193
[45] Date of Patent: Nov. 9, 1999

[54] PATIENT'S NURSING APPARATUS AND NURSING SYSTEM

[75] Inventors: Pekka Heinonen; Harri Okkonen, both of Espoo, Finland

[73] Assignee: Nokia Mobile Phones Ltd., Espoo, Finland

[21] Appl. No.: 08/877,932

[22] Filed: Jun. 18, 1997

[30] Foreign Application Priority Data

Jun. 19, 1996 [FI] Finland ................................. 962554

[51] Int. Cl.⁶ ................................................ G06F 17/60
[52] U.S. Cl. ................................................ 705/2
[58] Field of Search ..................... 705/2, 1, 28; 235/380, 235/381, 382, 385; 368/10, 12, 281; 364/479.01, 479.12

[56] References Cited

U.S. PATENT DOCUMENTS

| | | | |
|---|---|---|---|
| 4,483,626 | 11/1984 | Noble | 368/10 |
| 4,768,176 | 8/1988 | Kehr et al. | 368/10 |
| 4,911,327 | 3/1990 | Shepherd et al. | 221/3 |
| 5,347,453 | 9/1994 | Maestre | 705/2 |
| 5,774,865 | 6/1998 | Glynn | 705/2 |
| 5,802,014 | 9/1998 | Danko | 368/10 |
| 5,805,051 | 9/1998 | Herrmann et al. | 340/309.4 |

FOREIGN PATENT DOCUMENTS

| | | |
|---|---|---|
| 0709087 A1 | 5/1996 | European Pat. Off. . |
| 500160 | 4/1994 | Sweden . |
| 2205306 | 12/1988 | United Kingdom . |
| 2285433 | 7/1995 | United Kingdom . |

*Primary Examiner*—Frantzy Poinvil
*Assistant Examiner*—Alexander Kalinowski
*Attorney, Agent, or Firm*—Perman & Green, LLP

[57] ABSTRACT

The object of the present invention is a patient's nursing apparatus (2), which comprises reminding devices (4) for transmitting a predetermined reminding signal to a user of the apparatus at a predetermined point of time. In order that the carrying out of the activities, relating to the nursing of the patient, at the right time would be more efficient, the nursing apparatus comprises a storage space (7) for storing medication (8) needed for nursing the patient, feeding device (9) for feeding at least one medication items (8), located in the storage space, from the storage space (7) into a space of use (11) and detecting device (10) for detecting the at least one of the medication (8) located in the space of use, whereupon the reminding devices (4) are responsive to the detecting devices (10) for transmitting said predetermined reminding signal to the user of the apparatus (2) at a determined point of time, the detecting device (10) indicating that said at least one medication (8) is located in the space of use. The nursing apparatus is portable and it has been combined with a mobile station (1) for communicating information relating to the nursing apparatus. The nursing apparatus can be combined with a battery and be adapted to be connected to the battery space of a mobile station.

7 Claims, 1 Drawing Sheet

PATIENT'S NURSING APPARATUS AND NURSING SYSTEM

FIELD OF INVENTION

The object of the present invention is a patient's nursing comprising reminding for transmitting a predetermined reminding signal to a user of the apparatus at a predetermined point of time, a storage space for storing nursing means needed for nursing the patient, feeding means for feeding at least one nursing means located in the storage space into a space of use, and detecting means for detecting removal of the at least one nursing means located in the space of use, and the reminding means have been arranged to transmit the predetermined reminding signal to the user of the apparatusat the predetermined point of time as a response to an indication from the detecting means that said at least one nursing means is unremoved. In addition, the object of the invention is a system for nursing a patient, the system comprising such a nursing apparatus, and a data processing system, at the disposal of a person treating the patient, wherein data on the treatment of the patient are maintained.

BACKGROUND OF THE INVENTION

This invention relates in particularly to the medication of a patient and, more accurately, to a nursing apparatus, which helps the patient to remember when he should take his medicine. However, it will be appreciated that the nursing apparatus and system, according to the present invention, can also be utilised for other reminding purposes than merely reminding of the point of time when medicine should be taken. For example, a diabetic can utilise the nursing apparatus, according to the invention, to make it easier for him to remember the points of time when he should measure the glucose content of his blood. However, the invention will be discussed in the following, by way of example, particularly by means of a patient's medication.

A solution is previously known for reminding a patient of the time when he should take his medicine, wherein a paging device is placed at the patient's disposal. By means of the paging device in question, information on the point of time when he should take his medicine is transmitted to the patient. In other words, at a predetermined point of time the paging device gives an audio signal, whereupon the patient understands that he should take his medicine.

The most significant weakness in the known solution mentioned above is that if the patient does not happen to be in the immediate vicinity of the paging device at the medication time, the patient will not hear the audio signal of the paging device, whereupon he may forget to take his medicine. Another weakness of this known solution is that the paging device adds to the number of things the patient has to carry with him. In other words, in addition to medicine bottles and similar things, the patient should also carry the paging device with him.

In addition, different kinds of medicine dispensers are previously known, which comprise compartments so that, for example, there is a separate compartment for each medication time, wherein the medicine intended to be taken at that particular point of time has been stored. The medication times in turn appear from the text marked in connection with the compartments (e.g., Tuesday: morning/afternoon/evening). Thus, the patient can see with one glance at the dispenser the next time when he should take his medicine. Correspondingly, the danger that the patient would take his medicine twice is avoided because when the patient has once taken his medicine at the determined medication time, the compartment in question is empty and, thus, no medicine can again be taken therefrom.

One of the most significant weaknesses of the known medicine dispenser presented above is that the patient has to remember, on his own initiate, to control the times when he should take his medicine. Naturally, this causes a danger that the medicine is not taken at the predetermined medication time, and it may happen that the medicine is taken considerably later than intended.

Another prior known dispenser is disclosed in U.S. Pat. No. 4,911,327, which has been arranged to be kept on a table, having trays for pills, and actuators for moving a pill from a tray into a pill hopper and activating a flashing light and a buzzer, which are deactivated when the pill hopper is opened for removing the pill. If the pill is not removed within a predetermined time a remote signal, e.g. a telephone call is activated. Also as an accessory to the dispenser is a remote alarm unit, which the user may carry with him/her. The dispenser includes a radio transmitter transmitting to the remote alarm unit, and it is deactivated when the pill hopper is opened. The drawback with this solution is that the range of the transmitter is limited and by the time the user gets a signal on his remote unit, his pills are in the dispenser.

SUMMARY OF THE INVENTION

The purpose of the present invention is to solve the problems presented above and to make the nursing of the patient more efficient by providing for use a nursing apparatus by means of which it is possible to facilitate the carrying out of the activities, related to the nursing of the patient, at the right time. This object is achieved by means of a nursing apparatus, according to the present invention, characterised in that it is portable and that it has been combined with a mobile station for communicating information relating to the nursing apparatus.

The invention is based on the idea that when the feeding means of the nursing apparatus feed, by the predetermined medication time, the medicine, intended for use at that particular point of time, into the space of use of the nursing apparatus and when the reminding means have been arranged to repeatedly send the reminding signal to the user of the apparatus until he has removed the medicine located in the space of use, one can make certain that the patient really gets the correct dose of medicine and that the medication time does not pass without the patient noticing it, although he is not in the vicinity of the nursing apparatus at the meciation time because, in that case, the nursing apparatus continues to give the reminding signal, in other words, e.g., an audio signal, until the space of use has been emptied. Thus, an advantage of the nursing apparatus, according to the present invention, is that by means of it it is easier than before to remember the correct medication time, that by means of it one can be certain that the patient gets exactly the right dose of medicine, and that the possibility that the medication time is forgotten because the patient has not been in the vicinity of the nursing apparatus at the medication time can be prevented.

In addition, the object of the invention is a system by means of which the nursing of the patient can be made more efficient. It is characteristic of the system, according to the present invention, that the nursing apparatus is portable and it has been combined with a mobile station for communicating information relating to the nursing apparatus with said data processing system.

In the system, according to the present invention, the nursing apparatus may send, by means of transmission means arranged in connection with it, the alarm, e.g., to a physician treating the patient or, e.g., to a next of kin of the patient, in case the patient, for some reason, forgets to take his medicine. Thus, the physician or said next of kin can take the necessary measures so that no danger would result from the forgotten medication.

In the system, according to the present invention, the nursing apparatus has been arranged to receive messages from the data processing at the disposal of a person treating the patient system over radio communication using the mobile station, whereupon the feeding and/or reminding means of the nursing apparatus are responsive to the information contained in said messages. Thus, for example, the physician treating the patient can change remote-controlled, e.g., from the data processing system of a hospital, the patient's medication, i.e., the times when the nursing apparatus reminds the patient to take the medicine and/or the doses of medicine, which the feeding means feed from the storage space into the space of use without the patient even being aware of the matter.

As the nursing apparatus has been combined with a mobile station such as mobile telephone of a cellular radio system or a two-way pager, which has been arranged to automatically call a predetermined number if the patient has not taken his medicine. Alternatively the nursing apparatus has been combined with a battery and has been adapted to be connected to the battery space of a mobile station for communicating information relating to the nursing apparatus via said mobile station, and the battery has been arranged to feed energy to the nursing apparatus and to the mobile station. These features of the invention make it possible, in cases of emergency, for the patient to establish a direct speech communication with the person treating him, whereupon instructions can be transmitted to the patient.

The preferred embodiments of the nursing apparatus and system, according to the present invention, will appear from the enclosed dependent claims 2–5 and 7–11.

BRIEF DESCRIPTION OF THE DRAWINGS

In the following, the invention will be discussed in more detail by means of a preferred embodiment according to the invention by referring to the enclosed figures, of which

DETAILED DESCRIPTION

Figure 1:
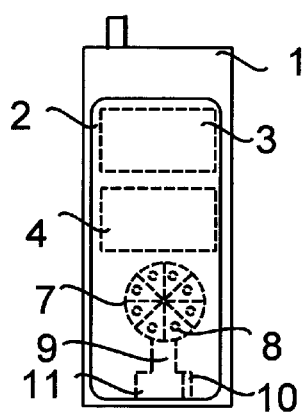
FIGS. 1 and 2 illustrate a first preferred embodiment of a nursing apparatus, according to the invention.
Figure 2:
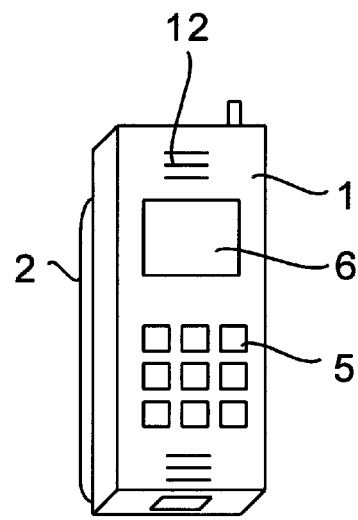

FIGS. 1 and 2 illustrate the first preferred embodiment of the nursing apparatus according to the invention. In the case, illustrated in FIGS. 1 and 2, the nursing apparatus has been connected to a mobile telephone 1 of a cellular radio system. In this embodiment, according to the invention, a nursing apparatus 2 has been fitted in the mobile telephone's battery space instead of an ordinary battery. Therefore, the nursing apparatus 2 also contains a battery, wherefrom the necessary energy for the use of the nursing apparatus 2 and the mobile telephone 1 is obtained.

In addition, in the nursing apparatus 2, there is a memory 4, wherein data concerning, among other things, the times when the patient should take his medicine, as well as data on what medicine the patient should take, have been stored. The contents of the memory 4 can be scanned by means of a keyboard 5 and a display 6.

Naturally, the mechanical structure of the nursing apparatus may vary considerably, and FIG. 1 only illustrates one possible structure. In the nursing apparatus, illustrated in FIG. 1, there is a medicine dispenser, which forms a storage space 7 for medicines 8. Naturally, if required, it is possible to arrange two separate dispensers in the nursing apparatus, which may contain medicines different to each other. Thus, by means of the nursing apparatus, it can be ensured that the patient gets two different medicines at the correct points of time.

When the nursing apparatus 2 detects, on the basis of the data stored in the memory 4, that the patient should take his medicine, it controls the medicine dispenser to rotate so that a predetermined compartment and the medicine tablet therein is placed by feeding means 9 so that the feeding means can convey the medicine tablet 8 from the dispenser 7 into a space of use 11. In the case, illustrated in FIG. 1, in the lower part of the space of use, there can be a hatch to be opened manually, through which the patient can remove the tablet located in the space of use.

A detector 10, located in the space of use 11, detects the tablet in the space of use, whereupon the nursing apparatus 2 starts to produce a determined audio signal utilising an alarm 12 intended for producing the ringing tone of the mobile telephone 1. When the ringing tone has been repeated a predetermined number of times, the nursing apparatus 2 sets up a connection, through the mobile telephone 1, to a predetermined number to call for help.

Figure 3:
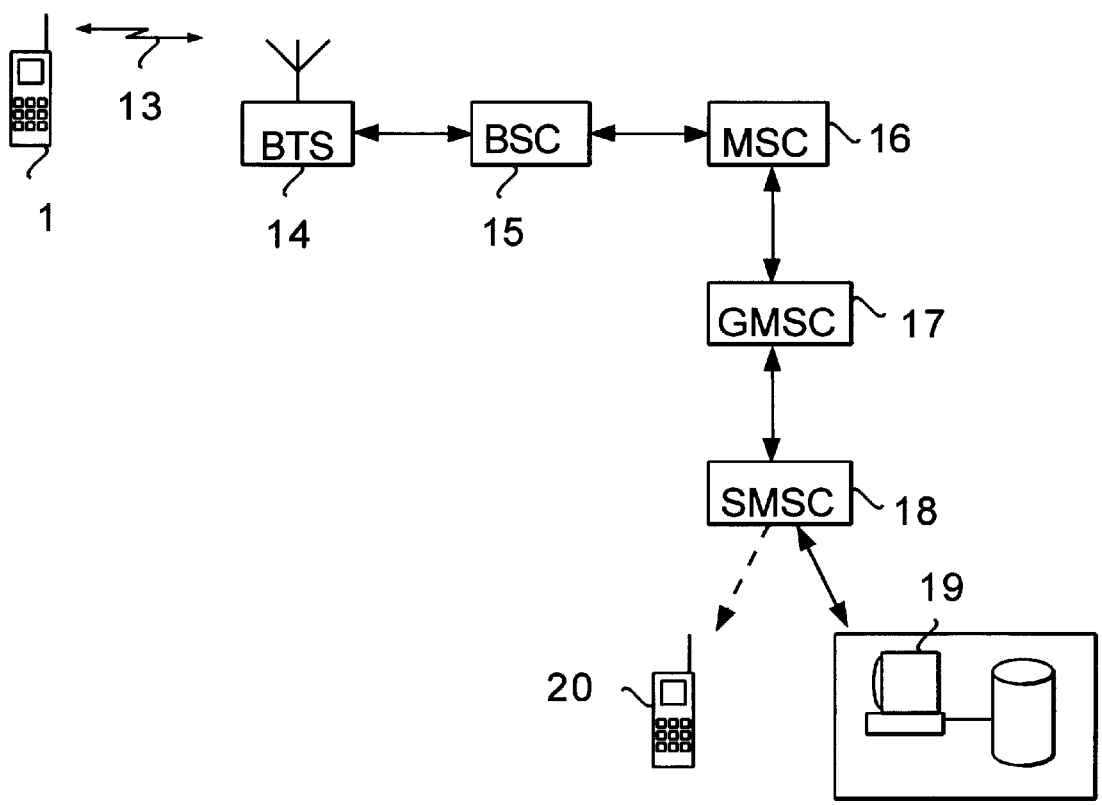
FIG. 3 illustrates a first embodiment of a system according to the invention.

FIG. 3 illustrates the first preferred embodiment of the system according to the invention. In the system, illustrated in FIG. 3, wherein the combined mobile telephone/nursing apparatus, presented in connection with FIGS. 1 and 2, is utilised, there can be, e.g., the GSM mobile telephone system.

In the case, illustrated in FIG. 3, the nursing apparatus can be arranged to transmit, through the mobile telephone 1, a short message to a data processing system 1, at the disposal of the physician treating the patient, always when the patient has taken his medicine or, alternatively, e.g., once a day, in which case, by means of one short message, the data concerning several medication times can be transmitted. Thus, the physician can follow the medication of the patient through the data processing system. In the case, illustrated in FIG. 3, the mobile telephone 1 transmits a short message 13 to a base station 14 using radio communication. The base station 14 transmits the message further, through a base station controller 15, a mobile services switching centre 16 and a gateway mobile services switching centre 17, to a short message service centre 18 (SMSC) of the mobile telephone system, wherefrom the message can be transmitted further, e.g., to a data processing system 19 of a hospital, or to a mobile telephone 20 of the person treating the patient. The GSM system and its short message service have been described in more detail, e.g., in the book "The GSM System for Mobile Communications", M. Mouly and M-B Pautet, Palaiseau, France, 1992, ISBN: 2-9507190-0-7 and, therefore, they will not be described more closely in this connection.

Correspondingly, the nursing apparatus may alert the physician or the patient's next of kin in case the nursing apparatus detects that the patient has not taken his medicine at the determined point of time. The alarm in question can be given either so that the nursing apparatus sets up, through the mobile telephone 1, a connection to a predetermined telephone number or, alternatively, e.g., transmits a short message to a mobile telephone 29 of the person treating the patient. In connection with the alarm, it is possible to transmit to the receiver of the alarm, e.g., a pre-recorded message informing the receiver of the alarm of what it is about and how he should act.

In the case, illustrated in FIG. 3, the physician treating the patient may change the patient's medication, if so required, from the data processing system 19 of the hospital, e.g., by sending a short message to the mobile telephone 1, wherefrom the data contained in the message are directed into the memory 4 of the mobile telephone 1. After this, the nursing apparatus utilises the new information stored in the memory for reminding and medicating the patient.

The specification presented above and the figures relating to it should only be considered illustrative of the present invention. It is obvious to persons skilled in the art that the invention can also be implemented in another form without deviating from the characteristics and scope of protection of the invention presented in the enclosed claims.

We claim:

1. A portable system for managing the administration of medication to a patient, said system using a radio communication system having a patient mobile station and a base station, said base station operatively associated with a data processing computer for entering, retaining and transmitting patient specific information related to a patient's medication, said portable system mounted on the patient mobile station for transport therewith comprising:

a storage compartment for containing a supply of medication needed for treatment of the patient;

a memory for receiving and storing data relative to the dispensing of medication from the data processing computer;

an alarm responsive to the memory to generate a signal, detectable by the patient, when a dosage of medication needs to be taken;

a dispenser responsive to the alarm signal for delivering a dosage of medication from the storage compartment to an access space for removal by the patient;

a detector adapted to sense the presence of the dosage of medication within the access space and to generate a signal relative to the presence or absence of the medication therein;

first means responsive to the detector signal to activate the mobile station and transmit a message to the base station for receipt by the data processing computer regarding the dispensing of medication; and second means responsive to the detector signal and the alarm signal to activate the mobile station and transmit a warning message when the medication is not removed from the access space within a predetermined period of time.

2. A portable system for managing the administration of medication to a patient as described in claim 1, wherein said radio communication system comprises a cellular phone network.

3. A portable system for managing the administration of medication to a patient as described in claim 1 wherein the base station has the further capability to transmit said warning messages received from the portable system to other mobile stations.

4. A portable system for managing the administration of medication to a patient as described in claim 1 wherein the base station has the further capability through the data processing computer to periodically modify the data stored in the patient mobile station memory.

5. A portable system for managing the administration of medication to a patient as described in claim 1 wherein the portable system further comprises a battery suitable for powering both the dispenser system and the mobile station, said portable system and said battery packaged to fit within the battery compartment of the mobile station.

6. A portable mobile station for managing the administration of medication to a patient, said station using a radio communication system having a mobile communication station and a base station, said base station being operatively associated with a data processing computer for entering, retaining and transmitting patient specific information related to a patient's medication, said portable patient mobile station comprising:

a storage compartment for containing a supply of medication needed for treatment of the patient;

a memory for receiving and storing data relative to the dispensing of medication from the base station computer;

an alarm responsive to the memory to generate a signal, detectable by the patient, when a dosage of medication needs to be taken;

a dispenser responsive to the alarm signal for delivering a dosage of medication from the storage compartment to an access space for removal by the patient;

a detector adapted to sense the presence of the dosage of medication within the access space and to generate a signal relative to the presence or absence of the medication therein;

first means responsive to the detector signal to activate the mobile station and transmit a message to the base station for receipt by the data processing computer regarding the dispensing of medication; and second means responsive to the detector signal and the alarm signal to activate the mobile station and transmit a warning message when the medication is not removed from the access space within a predetermined period of time.

7. A portable mobile station for managing the administration of medication to a patient, said station using a radio communication system having a mobile communication station and a base station, said patient mobile station comprising:

a storage compartment for containing a supply of medication needed for treatment of the patient;

a memory for receiving and storing data relative to the dispensing of medication;

an alarm responsive to the memory to generate a signal, detectable by the patient, when a dosage of medication needs to be taken;

a dispenser responsive to the alarm signal for delivering a dosage of medication from the storage compartment to an access space for removal by the patient;

a detector adapted to sense the presence of the dosage of medication within the access space and to generate a signal relative to the presence or absence of the medication therein;

first means responsive to the detector signal to activate the mobile station and transmit a message to the base station for receipt by the data processing computer regarding the dispensing of medication; and second means responsive to the detector signal and the alarm signal to activate the mobile station and transmit a warning message when the medication is not removed from the access space within a predetermined period of time; and wherein said storage compartment, memory, alarm, dispenser and detector are packaged with a battery suitable for powering the patient mobile station, said portable system and said battery packaged to fit within the battery compartment of the mobile communication station.

* * * * *